United States Patent
Ryan

[19]

[11] Patent Number: 5,954,313
[45] Date of Patent: Sep. 21, 1999

[54] MEDICAL INTRAVENOUS ADMINISTRATION LINE CONNECTORS HAVING A LUER ACTIVATED VALVE

[75] Inventor: Dana Wm. Ryan, Woodward, Okla.

[73] Assignee: Rymed Technologies, Inc., Woodward, Okla.

[21] Appl. No.: 08/841,281

[22] Filed: Apr. 29, 1997

Related U.S. Application Data

[63] Continuation-in-part of application No. 08/581,057, Dec. 29, 1995, Pat. No. 5,788,215.

[51] Int. Cl.$^6$ ........................................................ A61M 5/00
[52] U.S. Cl. ......................... 251/149.1; 604/167; 604/256
[58] Field of Search ..................................... 604/167, 247, 604/249, 256; 251/149.1; 137/511, 515

[56] References Cited

U.S. PATENT DOCUMENTS

| | | | |
|---|---|---|---|
| 3,192,949 | 7/1965 | De See. | |
| 3,799,171 | 3/1974 | Patel. | |
| 3,806,086 | 4/1974 | Cloyd | 251/149.7 |
| 3,831,629 | 8/1974 | Mackal et al. | 137/525 |
| 4,103,686 | 8/1978 | LeFevre | 251/139 X |
| 4,349,021 | 9/1982 | Raible | 128/214 R |
| 4,559,043 | 12/1985 | Whitehouse et al. | 604/201 |
| 4,617,015 | 10/1986 | Foltz | 604/100 |
| 4,681,132 | 7/1987 | Lardner | 137/271 |
| 4,683,916 | 8/1987 | Raines | 137/854 |
| 4,723,550 | 2/1988 | Bales et al. | 128/344 |
| 4,776,369 | 10/1988 | Lardner et al. | 137/515.5 |
| 4,908,018 | 3/1990 | Thomsen | 604/83 |
| 4,915,687 | 4/1990 | Sivert | 604/83 |
| 4,934,655 | 6/1990 | Blenkush et al. | 251/149.1 |
| 5,024,657 | 6/1991 | Needham et al. | 604/85 |
| 5,085,645 | 2/1992 | Purdy et al. | 604/167 |
| 5,108,380 | 4/1992 | Herlitze et al. | 604/283 |
| 5,116,021 | 5/1992 | Faust et al. | 251/149.1 |
| 5,163,922 | 11/1992 | McElveen, Jr. | 604/249 |
| 5,181,913 | 1/1993 | Erlich | 604/263 |
| 5,181,921 | 1/1993 | Makita et al. | 606/195 |
| 5,195,967 | 3/1993 | Nakao et al. | 604/83 |
| 5,199,947 | 4/1993 | Lopez et al. | 604/56 |
| 5,201,725 | 4/1993 | Kling | 604/284 |
| 5,203,775 | 4/1993 | Frank et al. | 604/256 |
| 5,215,538 | 6/1993 | Larkin | 604/249 |
| 5,217,434 | 6/1993 | Arney | 604/99 |
| 5,230,706 | 7/1993 | Duquette | 604/83 |
| 5,242,393 | 9/1993 | Brimhall et al. | 604/82 |
| 5,242,423 | 9/1993 | Goodsir et al. | 604/905 |
| 5,242,432 | 9/1993 | DeFrank | 604/284 |
| 5,250,028 | 10/1993 | Theeuwes et al. | 604/85 |
| 5,250,034 | 10/1993 | Appling et al. | 604/164 |
| 5,251,873 | 10/1993 | Atkinson et al. | 251/149.1 |

(List continued on next page.)

*Primary Examiner*—Kevin Lee
*Assistant Examiner*—Bryan C. Wallace
*Attorney, Agent, or Firm*—David P Gordon; David S. Jacobson; Thomas A. Gallagher

[57] ABSTRACT

Medical intravenous administration connectors according to a first embodiment include a first coupling member having a female luer, a valve member having a substantially rigid stem and a substantially resilient body with a sealing surface, and a second coupling member having a fluid coupling extending from one end and an internal valve member support. The coupling members are structured to couple to each other with the valve member being biased to a closed position. When assembled, the valve stem extends into the female luer, and the valve body biases the sealing surface against an annular ring in the first coupling member thereby blocking fluid communication. Vanes are provided in the second coupling member on which the resilient body of the valve sits, with the vanes acting as a centering mechanism for the valve. The valve is opened for fluid flow through the assembly by coupling a male luer to the female luer of the assembly. According to a second embodiment, the valve stem is replaced by a dome-like protrusion on the resilient valve body. The valve of the second embodiment is opened by applying fluid under pressure through the female luer. According to a third embodiment, the valve is partially rigid and partially resilient. All embodiments are easy to prime, limit priming volume, and are arranged without dead-spaces in which blood can be trapped.

12 Claims, 8 Drawing Sheets

U.S. PATENT DOCUMENTS

| | | | |
|---|---|---|---|
| 5,259,839 | 11/1993 | Burns | 604/96 |
| 5,269,771 | 12/1993 | Thomas et al. | 604/213 |
| 5,280,876 | 1/1994 | Atkins | 604/905 |
| 5,284,475 | 2/1994 | Mackal | 604/247 |
| 5,289,849 | 3/1994 | Paradis | 137/606 |
| 5,290,263 | 3/1994 | Wigness et al. | 604/247 |
| 5,300,033 | 4/1994 | Miller | 604/167 |
| 5,300,044 | 4/1994 | Classey et al. | 604/250 |
| 5,308,334 | 5/1994 | Sancoff | 604/131 |
| 5,322,518 | 6/1994 | Schneider et al. | 604/247 |
| 5,330,435 | 7/1994 | Vaillancourt | 604/167 |
| 5,334,170 | 8/1994 | Moroski | 604/80 |
| 5,336,174 | 8/1994 | Daoud et al. | 604/30 |
| 5,336,192 | 8/1994 | Palestrant | 604/167 |
| 5,338,313 | 8/1994 | Mollenauer et al. | 604/249 |
| 5,353,837 | 10/1994 | Faust | 137/614.18 |
| 5,356,375 | 10/1994 | Higley | 604/30 |
| 5,360,413 | 11/1994 | Leason et al. | 604/249 |
| 5,364,371 | 11/1994 | Kamen | 604/251 |
| 5,370,624 | 12/1994 | Edwards et al. | 604/169 |
| 5,390,898 | 2/1995 | Smedley et al. | 251/149.6 |
| 5,391,150 | 2/1995 | Richmond | 604/111 |
| 5,395,348 | 3/1995 | Ryan | 604/247 |
| 5,399,171 | 3/1995 | Bowman et al. | 604/247 |
| 5,401,255 | 3/1995 | Sutherland et al. | 604/247 |
| 5,405,323 | 4/1995 | Rogers et al. | 604/53 |
| 5,464,938 | 11/1995 | Werge et al. | 251/149.1 |
| 5,535,771 | 7/1996 | Purdy et al. | 137/15 |
| 5,578,059 | 11/1996 | Patzer | 604/249 |

MEDICAL INTRAVENOUS ADMINISTRATION LINE CONNECTORS HAVING A LUER ACTIVATED VALVE

This application is a continuation-in-part of my application Ser. No. 08/581,057, filed Dec. 29, 1995, U.S. Pat. No. 5,788,215 the complete disclosure of which is hereby incorporated by reference herein.

BACKGROUND OF THE INVENTION

1. Field of the Invention

This invention relates to medical IV administration line connectors. More particularly, this invention relates to needleless injection ports for the safe infusion and/or aspiration of fluids in intravenous and blood administration therapy.

2. State of the Art

Intravenous therapy has a long history of use in supplying patients with pharmaceuticals, liquid nourishment, or blood products. Prior art FIGS. 1 through 4 show that the current or conventional way of introducing parenteral liquid solutions and/or blood and blood products into a patient is by the conventional gravity feeding system 10. The feeding system 10 includes a container 12 that is either a bottle or bag for the parenteral solution, a tube 14 extending from the bottle or bag and connected to a Y-injection site 16 (piggyback or secondary Y-injection site), and a tube 18 from the Y-injection site 16 to a needle or catheter 20 which is inserted into a vein in the arm 22 of the patient. The vein-access needle or catheter is taped to the patient with adhesive tape 24 so that the chance of a detachment and disconnect from the vein is minimized.

Supplemental intravenous therapy from a piggyback or secondary bottle or bag 26 is introduced through the Y-injection site 16 into the primary intravenous administration set 10. As seen best in FIG. 3, the Y-injection site 16 which is integrated into the primary intravenous administration set 10 consists of two tubular conduits 16a, 16b which merge into a third tubular conduit 16c. The tubing 12 from the bottle or bag of parenteral solution of the primary intravenous administration set 10 is attached into the inlet port 16a of the Y-injection site. In similar fashion, the tube 18 is attached into the exit port 16c of the Y-injection site. A sealed entry port segment 17 of the Y-injection site 16 is provided by the extension conduit 16b which has a standard, self-sealing latex rubber septum 17a at its inlet port to seal this port from leakage. Consequently, it is difficult for pathogens to enter the Y-injection site 16 via the septum port 17 because of the seal 17a. This self-sealing septum 17a is of a conventional design and includes coaxial annular aprons which fit over the conduit wall and grip the external and internal wall surfaces to hold the septum securely to the conduit 16b. Typically, a plastic shrink-band (not shown) is shrunk on the outer wall of the septum 17a to securely connect it to the extension conduit 16b.

Figure 3:
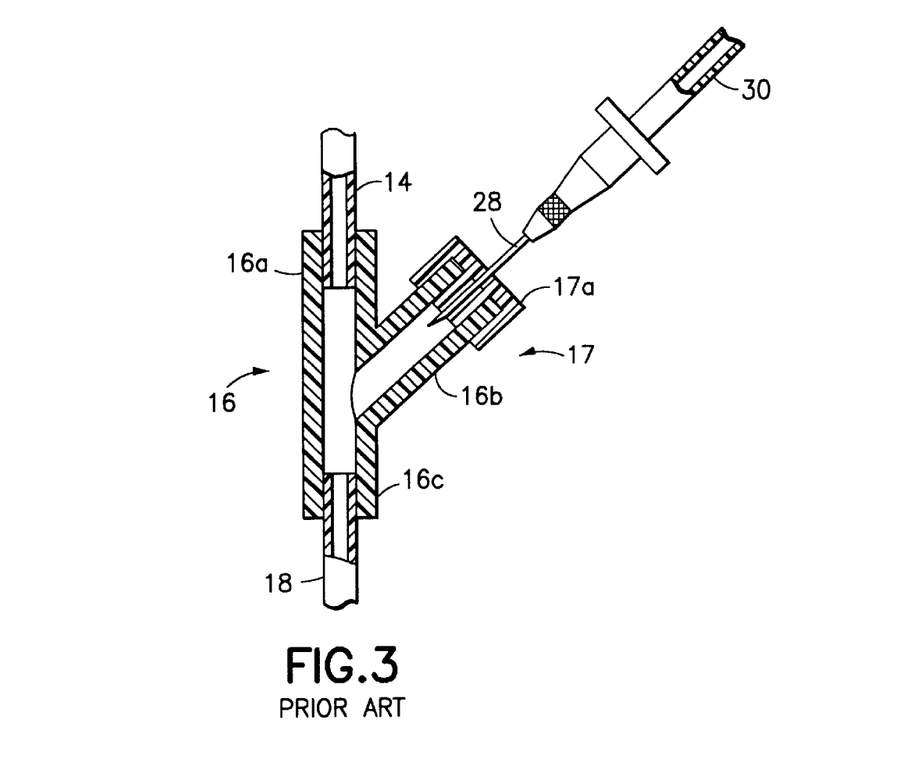
FIG. 3 is a broken side elevation view, in partial section, of a prior art Y-injection site.

The supplemental intravenous solution is introduced into the primary intravenous administration set 10 through the Y-injection site 16 by way of a primed piggyback or secondary intravenous set 26. The piggyback or secondary intravenous set 26 has a hollow-bore needle 28 attached to its distal end, which in turn is inserted through the self-sealing septum 17a of the Y-injection site 16 and into the extension conduit 16b. This needle 28 is connected to a tube 30 which is connected to a drip-chamber (not shown) of the piggyback or secondary intravenous set 26. A roller clamp 14a, 30a is typically used on both the primary and piggyback/secondary intravenous sets to control liquid flow rates into the patient.

There are several problems associated with the standard techniques employed for intravenous therapy. If the piggyback needle 28 is not securely taped to the Y-injection site 16 and the primary intravenous administration set tubing 12, 18, patients can move their arms, or roll over in bed accidentally pulling the needle 28 completely out of the septum 17a on the Y-injection site 16. If this occurs, the self-sealing latex septum 17a will close off automatically and not allow liquid or contamination to enter the primary intravenous administration set 10. The primary intravenous solution in the bottle or bag 12 will continue to flow into the patient, but, the necessary supplemental pharmaceutical solution from the piggyback or secondary bottle or bag 26 will no longer flow into the patient via the Y-injection site 16. The consequences to the patient for this situation can lead to serious complications and even death if the condition is not noticed by a clinician immediately. Even if the clinician notices the detachment of the needle 28 from the Y-injection site septum 17a immediately, the needle 28 is now contaminated with pathogens and should never be introduced back into the septum 17a. A new sterile, piggyback/secondary intravenous set must be opened, primed, and a new hollow-bore needle reinserted back into the septum on the Y-injection site. Additionally, whether the needle 28 is accidentally detached, or, the clinician removes the needle 28 from the Y-injection site septum once the supplemental pharmaceutical therapy is completed for the patient, the exposed needle 28 is contaminated with pathogens and must be safely disposed by the clinicians without accidentally sticking themselves.

To avoid accidental removal, the needle of the piggyback or secondary intravenous set may be taped to the Y-injection site and extension port. When this occurs, the needle may be secured from detachment, but the needle cannot be easily and safely removed by the clinician when the supplemental pharmaceutical therapy is completed, thereby creating a higher incidence for an accidental needle stick injury. Also, because clinicians hold the Y-injection site with one hand while the other hand is used to insert the needle into the Y-injection site septum, the clinicians may accidentally stick the needle directly into their hands holding the Y-injection site, or stick the needle completely through the Y-injection site wall into their hands.

Figure 1:
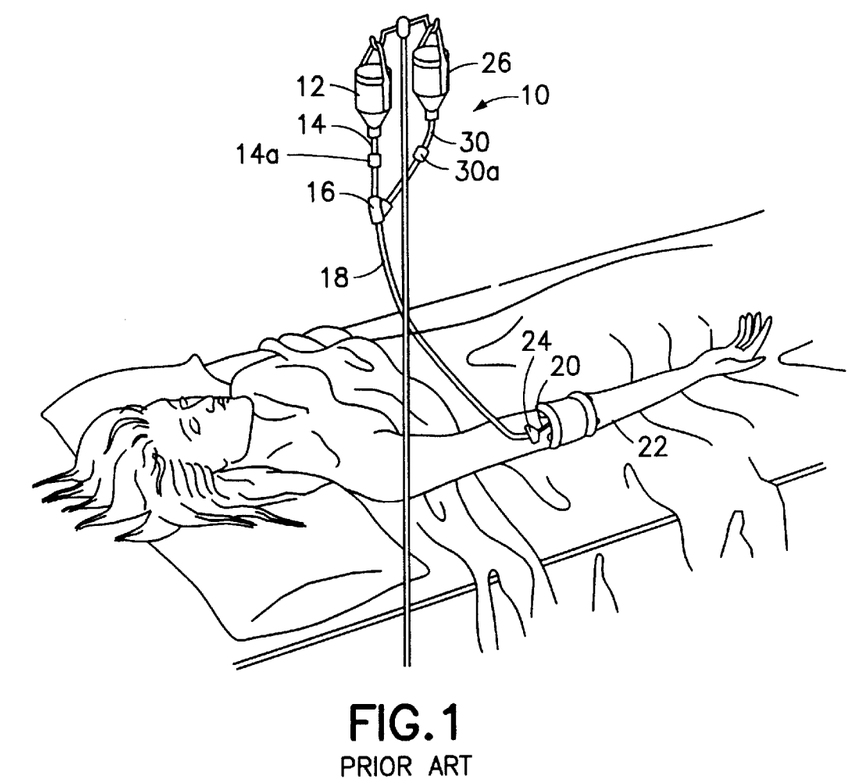
FIG. 1 is a schematic view of a prior art intravenous administration set coupled to a patient.
Figure 2:
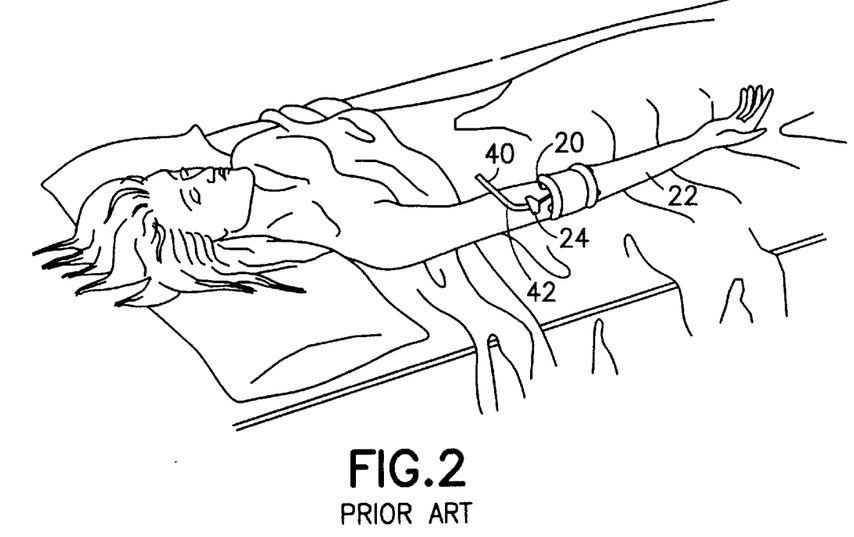
FIG. 2 is a view similar to FIG. 1 of a prior art "intermittent" intravenous administration set coupled to a patient.
Figure 4:
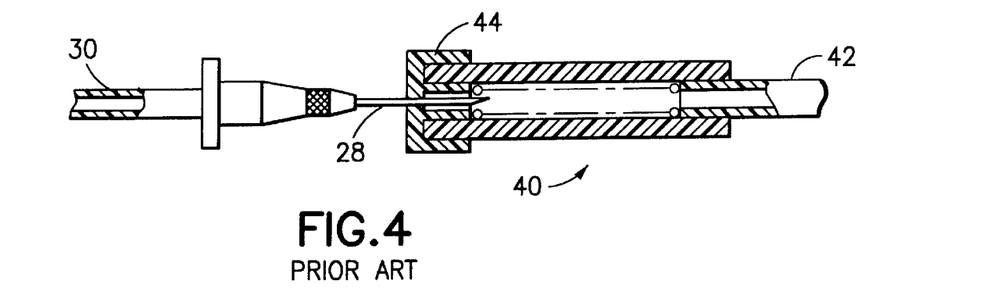
FIG. 4 is a broken side elevation view, in partial section, of a prior art heparin lock injection port.

The above description and problems associated with conventional continuous and supplemental intravenous therapy through a Y-injection site is similar to the problems associated with intermittent intravenous therapy using a "Heparin Lock" injection port 40 (FIGS. 2 and 4). A heparin lock injection port 40 is either connected directly to the vein-access device 20, or attached to a short catheter extension tubing set 42 typically with microbore tubing which is attached to the vein-access device as shown in FIG. 2. The heparin lock has a self-sealing septum port 44 which is similar to the septum port 17 described above. A conventional intermittent intravenous therapy could utilize a short-term primary intravenous administration set 26 with a hollow-bore needle 28 attached to the distal end of a tube 30. The needle would be inserted to the self-sealing septum found on standard heparin lock injection port 40. Another means of introducing supplemental intermittent pharmaceuticals to a patient is to perform an intravenous push utilizing a syringe with a hollow-bore needle attached. The drug is pushed into the patient through the heparin lock injection port 40. Once dispensed, the syringe/contaminated needle is removed from the self-sealing septum 44 on the heparin lock injection port 40.

As set out above, the common medical techniques for delivering supplemental liquid fluids to the patient necessitates the use of a hollow-bore needle. The needle is either attached to a secondary intravenous set or a syringe, and is inserted through the self-sealing rubber stopper on the heparin lock injection port or the Y-injection port that is integrated into the primary intravenous administration set. Typically, the needle is secured to the injection port only with tape. The needle can detach from the injection port resulting in a serious or fatal interruption of the flow of the intravenous solutions to the patient. Moreover, the exposed needle can easily be contaminated by contact with non-sterile objects. Sound aseptic techniques must be practiced by the healthcare professional in order to ensure that the sterile needle does not become contaminated and cause a nosocomial infection to the patient.

Since the discovery of the HIV virus that causes AIDS in the mid-1980's, a major concern among healthcare workers practicing the standard methods of delivering intravenous therapy is accidental needle sticks with a contaminated needle. When a needle is removed from an injection port, it may be contaminated with the patient's blood. The contaminated needle must be carefully disposed in a sharps container. While handling the needle during removal and disposal, clinicians may, and often do, inadvertently stick themselves. Among all of the needled medical devices used in healthcare facilities, contaminated intravenous needles are responsible for the most accidental needlestick injuries. When a needlestick injury occurs, the clinician must stop work and have a blood test performed. Since a needlestick injury can result in fatal disease, the injured clinician will also experience tremendous emotional trauma.

There is a wealth of prior art concerned with the problem of accidental needlesticks. Needleless valves are known in the art of intravenous administration. My prior U.S. Pat. No. 5,395,348 discloses a needleless intravenous quick connect/disconnect assembly which includes a first cylindrical member having a female luer connector extending from one end and providing a fluid path to the interior of the first cylindrical member, wherein a first seat is formed in the first cylindrical member at the junction of the female luer and the cylindrical opening; a second cylindrical member having a male-luer connector extending from one end and providing a fluid path to the interior of the second cylindrical member, wherein a second seat is formed in the second cylindrical member at the junction of the male-luer and the cylindrical opening; and a valve member having an integral stem, sealing surface, and resilient one-piece body. In the assembled state, the stem of the resilient valve member extends into the female luer from the inside of the first cylindrical member, and the resilient body of the valve member engages the second seat in the second cylindrical member and biases the sealing surface against the first seat in the first cylindrical member, thereby blocking fluid communication between the female-luer and the interior of the first cylindrical member. The integral valve member is a stepped diameter cylinder having a hollow body and solid stem. The body has a larger diameter than the stem and the step between the body and the stem is frustroconical wherein the sealing surface is formed. The end of the stem is provided with a diametrical slot. An annular fluid passage exists between the valve member body and the cylindrical members. The second seat is preferably formed from a plurality of radically arranged vanes which enter the hollow body of the valve member and flare outward from it. Spaces between the vanes provide a fluid passage from the male-luer to the annular fluid passage surrounding the valve member body. When a male-luer is inserted into the female luer connector, the valve member stem is pressed partially into the first cylindrical member thereby moving the sealing surface away from the first seat and also moving either the diametrical slot in the valve member stem at least partially inside the first cylindrical member. Fluid is free to pass from the male luer through the diametrical slot in the valve member stem, out into the first cylindrical member, around the sealing ring, into the annular fluid passage surrounding the valve member body, through the spaces between the radial vanes, and through the male luer connector in the second cylindrical member. When a male luer is withdrawn from the female luer connector, the resilient body of the valve member biases the valve stem back into the female-luer connector and thereby moves the sealing surface against the first seat, closing the valve.

Despite the many improvements in the connector disclosed in my U.S. Pat. No. 5,395,348, the valve member inhibits optimal performance of a needleless valve during intravenous and blood collection applications in several ways. Due to the variations of male luer connectors around the world, the one-piece resilient valve stem member can restrict fluid-flow, and the variation of fluid flow from one connector to another can resultingly be unacceptable. Further, the hollow body of the one-piece valve member does not permit optimal blood flushing of the valve, as the hollow body has an open end or concavity in which fluid may accumulate without passing along the flow-stream through the connector.

The device disclosed in the above-referenced parent application overcomes many of the shortcomings of the devices of my earlier patent. In the parent application, medical intravenous administration connectors are disclosed which include a first coupling member having a female luer, a valve member having a substantially rigid stem and a substantially resilient body with a sealing surface, and a second coupling member having a fluid coupling extending from one end and an internal valve member support. The coupling members are structured to couple to each other with the valve member being biased to a closed position. When assembled, the valve stem extends into the female luer, and the valve body biases the sealing surface against an annular ring in the first coupling member thereby blocking fluid communication. Preferably, vanes are provided in the second coupling member on which the resilient body of the valve sits, with the vanes acting as a centering mechanism for the valve. The valve may be opened for fluid flow through the assembly by coupling a male luer to the female luer of the assembly, or by pressure actuation. The connectors are easy to prime, limit priming volume, and are arranged without dead-spaces in which blood can be trapped. However, even with these advantages, it is still beneficial to improve the connectors by simplifying the manufacture of the connectors and enhancing their fluid flow performance.

SUMMARY OF THE INVENTION

It is therefore an object of the invention to provide a needleless medical injection port which is safe, efficacious, and easy to use.

It is also an object of the invention to provide an injection port valve system which is activated by any male luer connector without the use of adapters.

It is a further object of the invention to provide both luer activated and fluid pressure activated medical intravenous line connectors which achieve a high flow rate.

It is an additional object of the invention to provide luer activated medical intravenous line connectors which tolerate variations in male luer dimensions with little affect on the flow rate.

Another object of the invention is to provide both luer activated and fluid pressure activated medical intravenous line connectors which have good blood flushing characteristics.

A further object of the invention is to provide a medical IV line connector having a resilient valve member which is designed without "dead" spaces in which fluids may become entrapped.

An additional object of the invention is to provide luer activated medical intravenous line connectors with reduced priming volume relative to prior art luer activated medical intravenous line connectors.

A further object of the invention is to provide medical intravenous line connectors having components which are easily substituted during manufacture to provide either luer activated connectors or fluid pressure activated connectors.

Yet another object of the invention is to provide medical intravenous line connectors which are resistent to leaking even up to one hundred activations.

Still another object of the invention is to provide a medical IV line connector having a resilient valve member with means for repeatedly centering the valve relative to a sealing ring.

Even another object of the invention is to provide a medical IV line connector where debubbling is simply achieved.

It is still another object of the invention to provide a medical IV line connector which is easy to manufacture.

It is yet another object of the invention to provide a medical IV line connector having a resilient valve member which is functional under high pressure conditions.

In accordance with the objects stated above, a needleless IV line connector assembly is provided and a first (luer activated) embodiment thereof generally comprises: a first coupling member having a female luer connector (preferably a luer lock) with a fluid path therethrough, a flange having a first sealing ring seat formed therein and a first mating means; a second coupling member having a male luer connector (preferably a luer lock) extending from one end and providing a fluid path therethrough, the second coupling member having a second mating means; and a valve member including a valve stem and a resilient valve body having an annular sealing surface. A valve body seat is formed in the interior of the second coupling member by a plurality of radially arranged stepped vanes which extend substantially the entire length of the second coupling member above the male luer. The presently preferred valve body is substantially frustroconical tapering in diameter toward the male luer and having a relatively broad end with a stepped axial bore defining the annular sealing surface. The presently preferred valve stem has a stepped cylindrical portion which fits into the axial bore of the valve body and a pair of spaced apart upstanding members which extend into the female luer. The upstanding members preferably have curved outer surfaces and chamfered edges. A pair of inclined surfaces meet at a peak between the upstanding members and ramp outward toward the cylindrical portion of the valve stem.

The first embodiment of the connector assembly is assembled by snapping the stepped cylindrical portion of the valve stem to the stepped bore of the valve body, placing the valve body in the valve body seat of the second coupling member, placing the first coupling member over the valve stem so that the stem enters the female luer and the mating means on the flange on the first coupling member mates with the mating means of the second coupling member. While applying axial pressure to join the coupling members, sonic energy is applied to weld the mating means and hence the members together. Under the influence of sonic energy, the mating means melt at their point of contact and move towards each other to form a strong fluid-tight fusion. As assembled in this fashion, the valve body is stabilized, centered, and biased towards the first sealing ring.

In this luer-activated embodiment of the invention, the length of the female luer and/or the length of the upstanding members of the valve stem is chosen so that when a male luer is inserted into the female luer, the valve stem is pushed towards the male luer of the assembly thereby compressing the valve body by moving the sealing surface of the valve body away from the first seat. When the valve stem is purged, the inclined surfaces of the valve stem move at least partially inside the interior of the second coupling member. Fluid is thus free to pass through the space between the upstanding members of the valve stem along the inclined surfaces of the valve stem, through the spaces between the radial vanes, and through the male luer connector of the assembly. When opened, the valve member allows fluid flow in either direction, from the male luer to the female luer of the assembly or vice versa. When a male luer is withdrawn from the female luer connector, the resilient valve body expands and biases the valve stem back into the female luer connector and also moves the sealing surface against the first seat, closing the valve.

According to a second (fluid activated) embodiment of the connector assembly, the valve member includes a substantially frustroconical valve body having a knob or hemispherical bump on one end defining the annular sealing surface. No valve stem is used in the second embodiment, but the connector assembly is otherwise the same and is assembled in the same manner as the first embodiment. According to this embodiment, when a male luer is attached to the female luer connector of the assembly, fluid passing through the male luer with sufficient pressure causes the valve member to compress and move away from the sealing surface and allow the fluid to flow through the spaces between the radial vanes, and through the male luer connector of the assembly. When fluid ceases to be introduced, the valve member expands and moves the sealing surface against the first seat, closing the valve. In this embodiment, the valve member only allows fluid flow from the female luer to the male luer but not vice versa.

According to a third (fluid activated) embodiment of the invention, the valve member includes a resilient core which is insert molded in a relatively hard plastic frustroconical body. The resilient core has a substantially I-shaped cross section with a knob or hemispherical bump on one end defining an annular sealing surface. The relatively hard plastic frustroconical body defines an annular stopping surface surrounding the annular sealing surface of the resilient core which lies adjacent the flange of the female luer. Under extreme backpressure conditions (e.g., 1200 psi), the stopping surface prevents the valve member from being forced out of the connector assembly through the female luer.

According to other aspects of the invention, the second coupling member may be formed as a Y-site adapter rather than a male luer lock, and the third embodiment may be formed as a multiple access manifold coupled to a plurality of first coupling members and valve members.

Additional objects and advantages of the invention will become apparent to those skilled in the art upon reference to the detailed description in conjunction with the accompanying drawings.

DETAILED DESCRIPTION OF THE PREFERRED EMBODIMENTS

Figure 5:
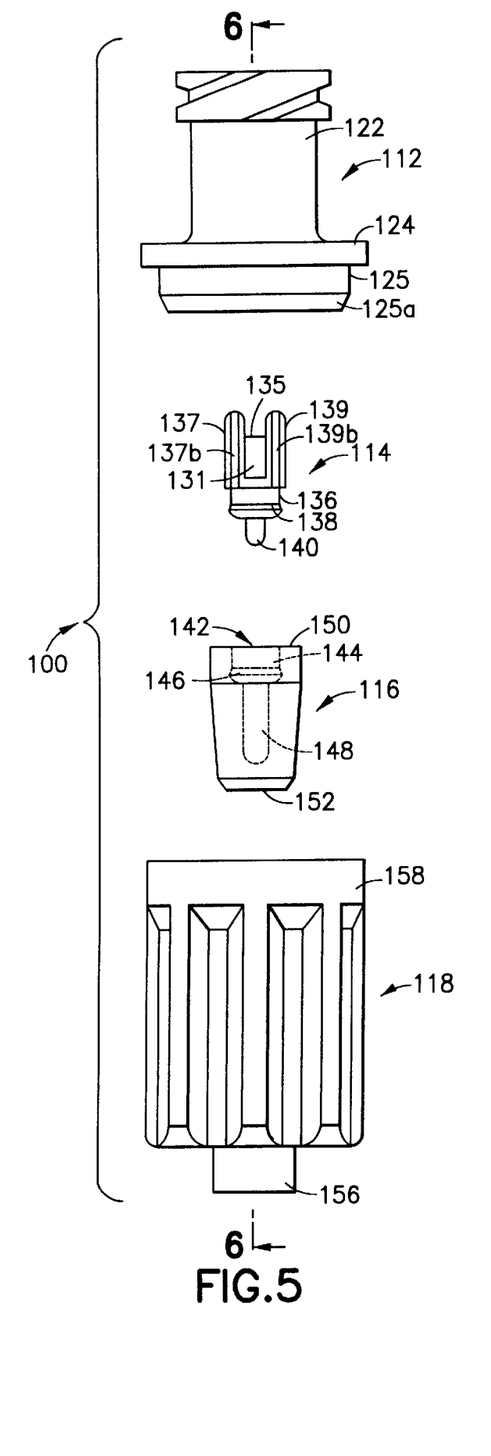
FIG. 5 is an exploded perspective view of a first embodiment of the invention.
Figure 6:
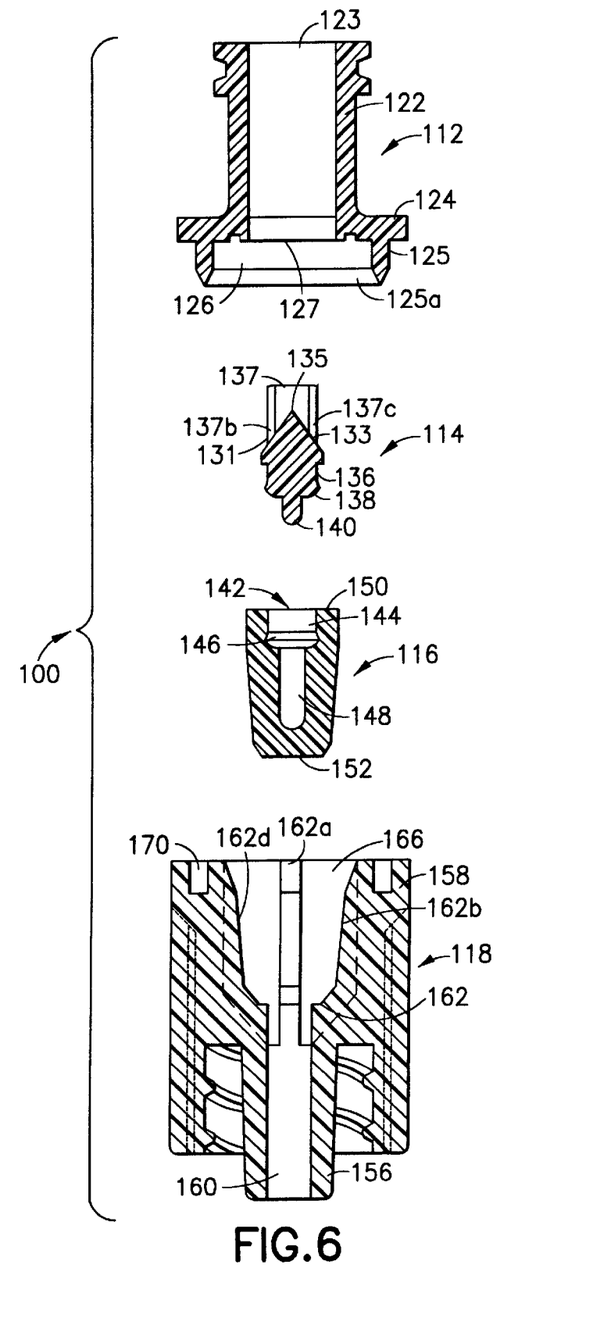
FIG. 6 is an exploded sectional view taken along line 6—6 in FIG. 5.
Figure 7:
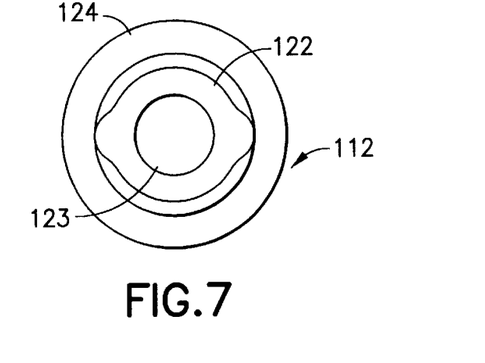
FIG. 7 is a top plan view of the first coupling member of FIGS. 5 and 6.

Turning now to FIGS. 5–7, a first embodiment of a connector assembly 100 according to the invention generally includes: a first coupling member 112, a valve stem 114, a resilient valve body 116, and a second coupling member 118. The first coupling member 112 is a female luer connector (preferably a luer lock) 122 having a flange 124 from which extends a cylindrical mating means 125 with a tapered edge 125a. The female luer connector 122 provides a fluid path 123 to the interior 126 of the cylindrical mating means 125. At the opening from the female luer into the cylindrical space 126, a first sealing ring seat 127 is formed.

Figure 8:
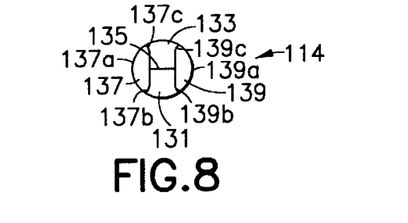
FIG. 8 is a top plan view of the valve stem of FIGS. 5 and 6.
Figure 9:
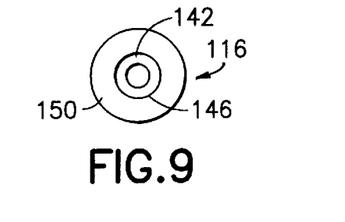
FIG. 9 is a top plan view of the valve body of FIGS. 5 and 6.
Figure 10:
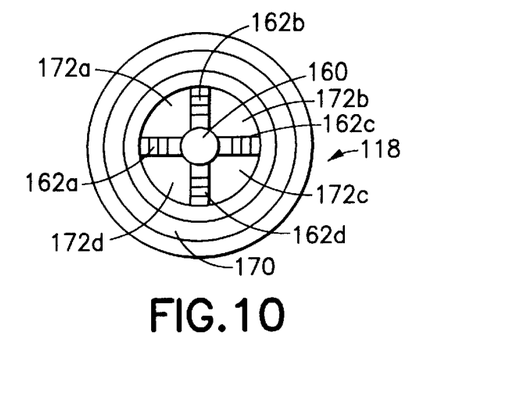
FIG. 10 is a top plan view of the second coupling member of FIGS. 5 and 6.

The valve stem 114 has a cylindrical portion 136 with a circumferential flange 138, and an axial stabilizing pin 40 at one end and a pair of spaced apart upstanding members 137, 139 at the other end. The upstanding members 137, 139 preferably have curved outer surfaces 137a, 139a and chamfered edges 137b, 137c, 139b, 139c. A pair of inclined surfaces 131, 133 meet at a central peak 135 between the upstanding members 137, 139 and ramp downward and outward toward the cylindrical portion 136 of the valve stem 114. According to a presently preferred embodiment, the angle defined by the central peak 135 is approximately 69°. This valve stem design according to the invention can be made easily and inexpensively by injection molding.

Figure 11:
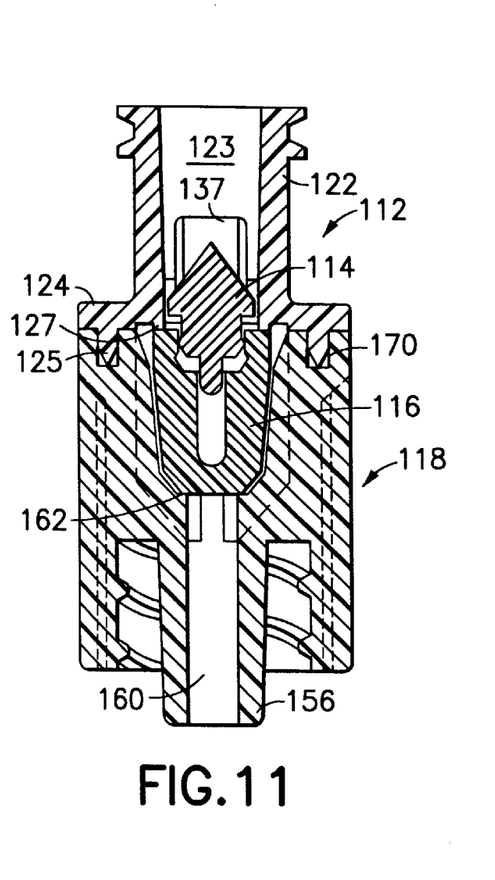
FIG. 11 is an assembled sectional view of the embodiment of FIGS. 5–10.
Figure 12:
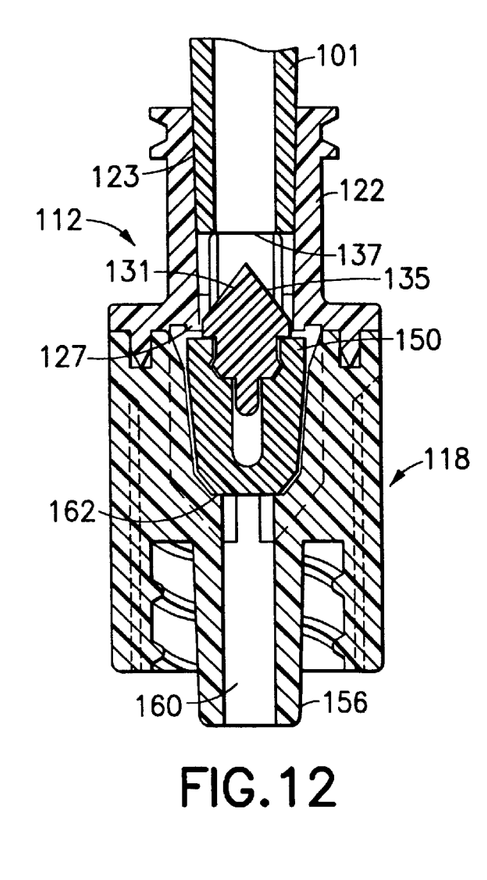
FIG. 12 is a view similar to FIG. 11 with an attached male luer forcing the valve member in the open position.
Figure 13:
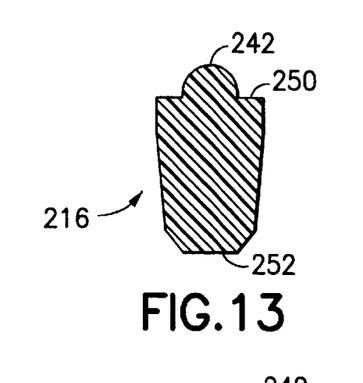
FIG. 13 is a sectional view of a valve member according to a second embodiment of the invention.
Figure 14:
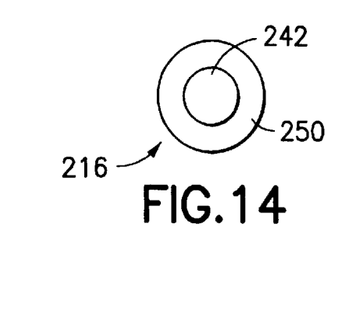
FIG. 14 is a top plan view of the valve member of FIG. 13.

The resilient valve body 116 is substantially frustroconical with a broader end serving as an annular sealing surface 150 and a narrower end 152. The annular surface 150 is defined by an axial bore 142. The axial bore 142 has a relatively large diameter portion 144 with an interior surface groove 146 and a relatively small diameter portion 148. The valve stem 114 and the valve body 116 snap together as shown in FIGS. 11 and 12. More specifically, the portion 144 of the bore 142 in the valve body 16 receives the cylindrical portion 136 of the valve stem 114. The circumferential flange 138 has a diameter slightly larger than the diameter of the portion 144 of the bore 142. When the stem 114 is inserted into the body 116, the flange 138 stretches the resilient body 116 until the flange reaches the groove 146 in the bore 142. The groove 142 has a diameter just slightly smaller than the diameter of the flange 138. The pieces snap together when the flange 138 embraces the groove 146, forcing the groove 146 to expand. This inhibits the pieces from separating. The axial stabilizing pin 140 of the valve stem 114 is received by the small diameter portion 148 of the bore 142. It should be noted that length of the pin 140 is shorter than the length of the small diameter portion 148 of the bore 142. Thus, when the stem is pushed into and compressed the valve body 116, the valve body can expand into the bore 142.

The second coupling member 118 has a male luer connector (preferably a luer lock) 156 at one end and an open ended cylinder 158 at the other end. The male luer 156 has an interior fluid path 160 which terminates in a valve body seat 162 inside the interior space 166 of the open ended cylinder 158. The valve body seat 162 includes a plurality of substantially stepped vanes 162a–162d which extend substantially along the entire length of the interior 166 of the cylinder 158 above the male luer 156. These vanes serve the function of consistently centering the valve in the seat after activation (see FIGS. 11 and 12), such that no leakage is experienced even after numerous (e.g., one hundred) activations. In addition, spaces 172a–172d between the vanes provide a flow path for fluid around the valve body as described below. An annular channel mating means 170 is provided at the end of the cylinder 158 and is dimensioned to receive the cylindrical mating means 125 of the first coupling member 112.

The connector assembly 100 of FIGS. 5–12 is assembled by inserting the stem 114 into the valve body 116 as described above, placing the body 116 of the valve member in the valve body seat 162 of the second coupling member 118, placing the first coupling member 112 over the valve stem 114 so that the stem enters the female luer 122 and the tapered edge 125a of the cylindrical mating means 125 rests inside the annular channel 170 of the second coupling member 118. While applying axial pressure to the first and second coupling members, the mating means and the first and second coupling members are welded by the application of sonic energy applied to weld the members together. Indeed, under the influence of sonic energy, the cylindrical members melt at their point of contact and move towards each other to form a string fluid-tight fusion. As assembled in this fashion, and as seen in FIG. 11, the valve body 116 is stabilized, centered, and biased towards the first sealing ring 127.

In use, as seen in FIG. 12, when a male luer 101 is inserted into the female luer 122 of the first coupling member 112, the valve stem 114 is pushed downward, causing the valve body to compress and causing the annular sealing surface 150 of the resilient valve body 116 to unseat from the sealing ring 127 of the first coupling member 112. When the valve is in the open position as shown in FIG. 12, fluid is able to flow from the male luer 101 along the inclined surfaces 131, 135 into the spaces 172a–172d (FIG. 10) between the vanes 162a–162d to the male luer 156. Similarly, according to this embodiment, when the male luer 101 is inserted as shown in FIG. 12, fluid is free to flow from the male luer 156 back to the female luer 122 and through the male luer 101. When the male luer 101 is removed from the female luer 122, the resilient valve body 116 expands and returns to the position shown in FIG. 11, sealing the valve so that no fluid can flow through the valve.

According to the invention, the arrangement of the vanes and the valve body permits repeated use with accurate reseating of the valve and no leakage. In addition, the geometry of the valve body, the vanes, and the valve stem provide very high flow rates with a very low priming volume. Also, the valve design avoids the presence of any "dead space" where biological fluids can accumulate and provide a host for pathogens. The entire fluid path is easily flushed. According to the presently preferred embodiment of the invention, the first coupling member 112 and the second coupling member 118 are made of clear plastic so that the clinician can observe aspiration and flushing. The presently preferred material for both coupling members as well as for the valve stem is BASF TERLUX #2802TR clear ABS. The presently preferred material for the resilient valve body is WACKER ELASTOSIL #LR-3003-50.

Figure 15:
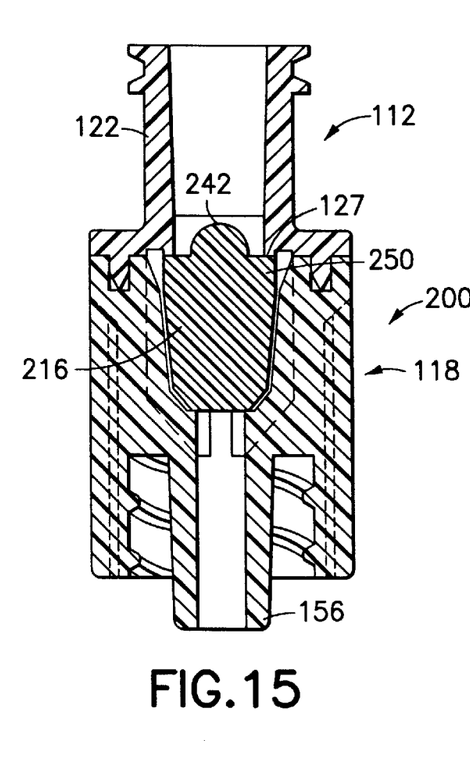
FIG. 15 is an assembled sectional view of a second embodiment of the invention utilizing the valve member of FIGS. 13 and 14.
Figure 16:
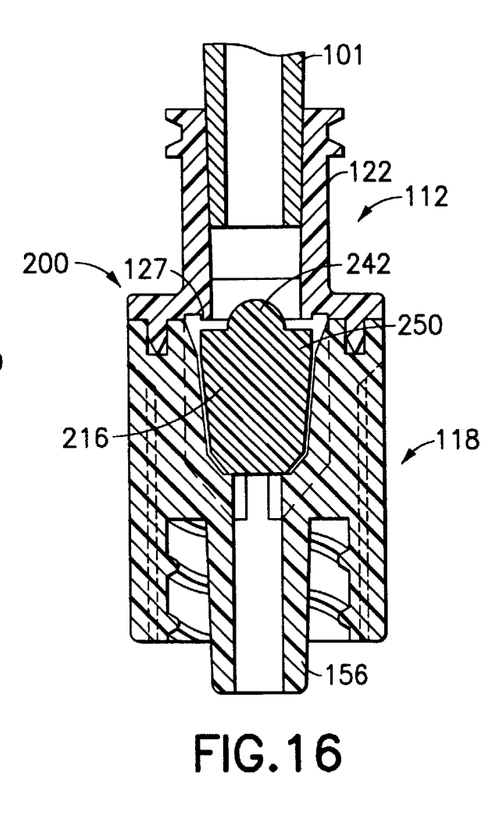
FIG. 16 is a view similar to FIG. 15 with an attached male luer showing the action of fluid pressure on the valve member.

Turning now to FIGS. 13–16, a second (fluid activated) embodiment of a connector assembly 200 according to the invention utilizes the same first and second coupling members 112, 118, but with a different valve member 216. In particular, the valve member 216 is comprised of a unitary resilient valve body, but does not include a valve stem. The valve body is substantially frustroconical with a broad end serving as a sealing surface 250 and a narrow end 252. The broad end also includes a centrally located dome 242 around which the annular sealing surface 250 is located. The valve body 216 does not utilize a valve stem. The connector assembly 200 is assembled in substantially the same manner as the connector assembly 100 described above, except that no assembly of the valve body and stem is required. When the connector is assembled as shown in FIG. 15, the valve body 216 is biased between the vanes of the coupling member 118 and the sealing ring 127 of the connector member 112. The dome 242 on the valve body 216 resides at the distal end of the female luer 122. When a male luer 101 is inserted into the female luer 122, the valve member 216 does not move and the fluid passage between the female luer 122 and the male luer 156 of the connector assembly 200 remains closed. Upon the introduction of a fluid through the male luer 101, however, fluid pressure acts upon the dome 242 and the annular surface 250 to compress the valve member 216 as shown in FIG. 16. This opens a passageway from the female luer 122 to the male luer 156. The valve member 216 will remain in this open position so long as fluid pressure is applied through the male luer 101. When pressure ceases, the valve member 216 will return to the closed position shown in FIG. 15. It will therefore be appreciated that according to this embodiment of the invention, fluid flow from the male luer 156 to the female luer 122 is virtually impossible as a pressure change to effect such flow will cause the valve member 216 to return to the closed position.

The connector assembly 200 provides the same advantages of low priming volume and high flow rate as the connector assembly 100 described above. While the valve member 216 is shown with a dome 242, the dome is not necessarily essential to the concept of the invention. The dome is preferred because it provides a greater surface area upon which fluid may act to compress the valve member. The presence of the dome, therefore allows the valve to be opened with a lower fluid pressure than would be required to open the valve without a dome. In addition, while the dome has been shown as an integral part of the valve body 216, a separate stem-like dome member could be inserted into the valve body 116 in the manner shown in FIGS. 5 and 6.

Figure 17:
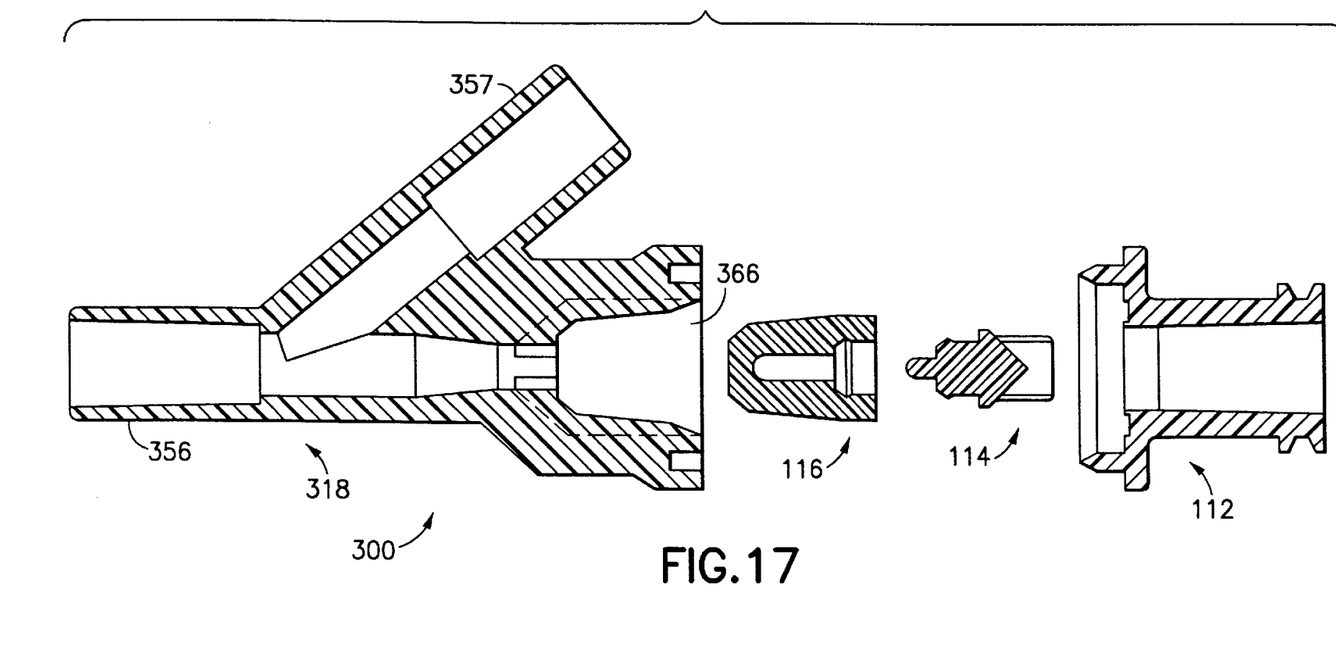
FIG. 17 is an exploded sectional view of a Y-site adapter according to the invention.

FIG. 17 shows a Y-site connector 300 based on the connector 100 described above. The Y-site connector 300 utilizes a first coupling member 112, a valve stem 114, a valve body 116, and a Y-site second coupling member 318 which replaces the second coupling member 118 shown in FIGS. 5 and 6. The end of the Y-site adapter 318 which couples with the first coupling member 112 and receives the valve body 116 is substantially the same as the second coupling member 118 described above. The other end of the Y-site adaptor 318 is provided with two fluid connectors 356, 357 which provide fluid paths in communication with each other as well as with the interior 366 of the coupling member 318. The Y-site connector 300 is assembled in substantially the same manner as the connector 100 described above.

Figure 18:
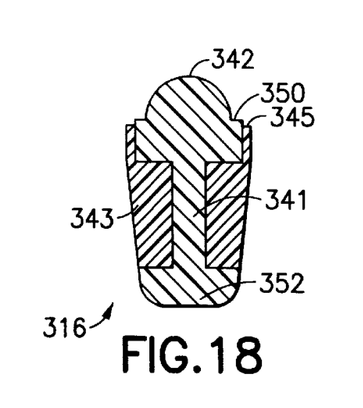
FIG. 18 is a sectional view of a valve member according to a third embodiment of the invention.
Figure 19:
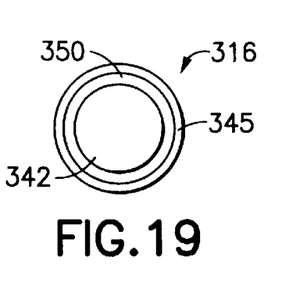
FIG. 19 is a top plan view of the valve member of FIG. 18.

Turning now to FIGS. 18 and 19, a valve body 316 according to a third embodiment of the invention includes a resilient core 341 which is insert molded in a relatively hard plastic frustroconical body 343. As presently preferred, the core 341 is made of silicone and the body 343 is made of polycarbonate. The resilient core 341 has a substantially I-shaped cross section with a knob or hemispherical bump 342 on one end defining an annular sealing surface 350. The other end 352 of the core 341 forms the narrow lower end of the valve body 316. The relatively hard plastic frustroconical body 343 defines an annular stopping surface 345 surrounding the annular sealing surface 350 of the resilient core 341. The overall shape and dimensions of the valve body 316 are substantially the same as those of the valve body 216 described above and the valve body 316 may be substituted for the valve body 216 in the connectors 200 or 300 described above. The relative dimensions of the resilient insert 341 and the outer body 343 are such that, when installed in a connector (e.g. 200 in FIGS. 15 and 16), the annular sealing surface 350 engages the sealing ring 127 (FIG. 15 and 16) in the same manner as the sealing surface 250 of valve body 216. In addition, however, the relative location of the stopping surface 345 is such that it lies outside the sealing ring adjacent to the lower surface of the flange 124 of the first coupling member 112. As shown in FIG. 18, the surface 350 is slightly raised above the surface 345. According to a presently preferred embodiment, the surface 350 is approximately 0.005–.010 inch higher than the surface 345. The advantage of the hard stopping surface 345 is best understood with reference to FIG. 20 wherein the valve body 316 is utilized in a multiple access manifold 400.

Figure 20:
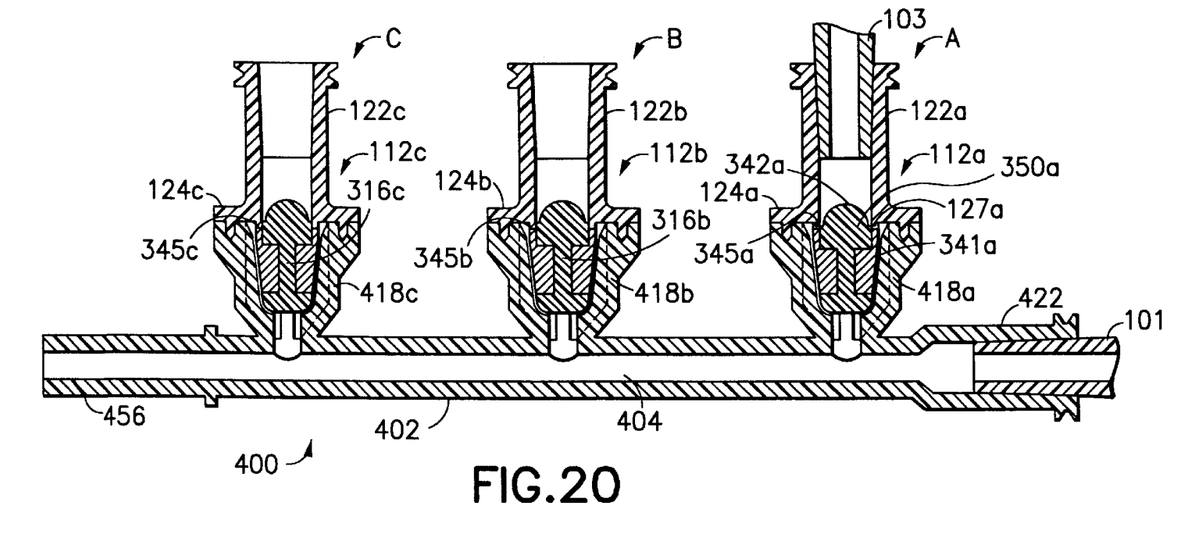
FIG. 20 is an assembled sectional view of a third embodiment of the invention utilizing the valve member of FIGS. 18 and 19.

Turning now to FIG. 20, a multiple access manifold 400 according to the invention includes a body 402 having a throughbore 404 with a male luer 456 at one end thereof and a female luer 422 at the other end thereof. Three coupling member-valve body assemblies (A–C) are arranged along the manifold body 402 as shown. The manifold 400 is often used in relatively high pressure applications. It has been discovered that when fluid under high pressure is applied to the female luer 422 (via a male luer 101), the back pressure created at the valve bodies 316a–316c is substantial. If the fully resilient valve body 216 (FIG. 13) is used in a manifold assembly of this type, high back pressure can cause the valve bodies to be forced into the female luers 122a–122c and under extremely high pressure, the valve bodies can be blown out of the manifold. With the partially rigid valve body 316, however, the hard stopping surface 345 prevents the valve body from entering the female luer and also prevents the sealing ring from damaging the sealing surface 350 of the resilient portion of the valve body 316. As shown in FIG. 20, the resilient portion 341a of the valve member 316a is compressed under the influence of fluid pressure entering via the luer 103 (which pressure is greater than the pressure of fluid entering through luer 101). In this compressed state, the annular sealing surface 350a of the valve member 316a is moved away from the sealing ring 127a of the coupling member 112a and allows fluid to flow as described hereinabove. If the fluid introduced via the luer 101 (or via the luer 103) is under high pressure and significant back pressure is created at the valve members 316b, 316c (and 316a if no pressure is applied through luer 103), the hard stopping surfaces 345b, 345c, (345a) will abut the inner surfaces of the flanges 124b, 124c, (124a) and prevent the valve members 316b, 316c, (316a) from being forced out into the female luers 122b, 122c (122a).

There have been described and illustrated herein several embodiments of medical IV administration line connectors. While particular embodiments of the invention have been described, it is not intended that the invention be limited thereby, as it is intended that the invention be as broad in scope as the art will allow. Thus, it will be appreciated by those skilled in the art that the term "IV fluid" is intended to be understood in a broad sense to include blood, blood products, dyes, or other fluids and the term "administration" is used in its broad sense to include the dispensing or collection of the "IV fluid". Further, while the connectors are illustrated as preferably having a female luer lock on one end, and a male luer lock on the other end, it will be appreciated that, although not preferred, simple luer slips could be utilized in lieu of luer locks. It will also be understood that while one end of the connector must be a female coupling, it is not necessary that the other end of the connector be a male coupling. Moreover, while certain embodiments connector assembly have been shown as having two cylindrical portions, one of which fits inside the other, it will be appreciated that either cylindrical portion could extend around the other provided that a cylindrical space is established for the biased valve member. In addition, while the valve member seat has been disclosed as having four radial vanes, it will be understood with the benefit of the instant disclosure that the essence of the valve member seat is to provide a stable support and centering for the valve member body while also providing a fluid path into the male luer. Other types of valve member seats having these features could be substituted without departing from the spirit of the invention. Furthermore, while a single path luer connector and a Y-site connector have been shown, it will be appreciated that the principles of the invention may also be applied to manifold connectors and the like as disclosed in my earlier patents and applications. Therefore, it will be appreciated by those skilled in the art that yet other modifications could be made to the provided invention without deviating from its spirit and scope as so claimed.

I claim:

1. A fluid line connection assembly for coupling to and uncoupling from a first fluid pathway which terminates in a first male luer, the fluid line connection assembly comprising:
   a) a first coupling member having a first female luer at a first end of said first coupling member, and a first mating structure;
   b) a valve member having a stem and a resilient body with a sealing surface, said valve member disposed relative to said first coupling member with said stem extending into said first female luer, said stem having a pair of spaced apart upstanding members and a pair of inclined surfaces meeting at a peak between said upstanding members, said inclined surfaces being arranged to direct fluid flow radially outward from between said upstanding members; and
   c) a second coupling member having an open generally cylindrical chamber with a valve member support, a first fluid coupling member in fluid communication with said cylindrical chamber, a valve member support, and a second mating structure for mating and coupling with said first mating structure, said second coupling member being coupled to said first coupling member with said valve member support supporting said resilient body of said valve member such that said sealing surface is biased against said first female luer thereby blocking fluid communication between said female luer and said first cylindrical chamber.

2. A fluid line connection assembly according to claim 1, wherein:
   said first female luer and said stem extending into said first female luer are sized such that,
   upon coupling the first male luer to said first female luer, the first male luer engages said stem and moves said stem toward said second coupling member, thereby compressing said resilient body, moving said sealing surface away from said female luer, and opening fluid communication between said female luer and said cylindrical chamber, and
   upon uncoupling the first male luer from said first female luer, the first male luer disengages said stem and said resilient body expands towards said female luer such that said sealing surface contacts said female luer and blocks fluid communication between said female luer and said cylindrical chamber.

3. A fluid line connection assembly according to claim 1, wherein:
   said upstanding members each have a curved surface and a chamfered edge.

4. A fluid line connection assembly according to claim 1, wherein:
   said stem and said resilient body are separate mating pieces, and
   said stem is relatively rigid compared to said resilient body.

5. A fluid line connection assembly according to claim 4, wherein:
   said stem is formed from a substantially rigid material.

6. A fluid line connection assembly according to claim 1, wherein:

said valve member support includes a fluid passage in fluid communication with said first fluid coupling member.

7. A fluid line connection assembly according to claim 6, wherein:

said valve member support comprises a plurality of radial vanes and said fluid passage comprises a space between said radial vanes.

8. A fluid line connection assembly according to claim 7, wherein:

said radial vanes have steps and said resilient body is supported by said steps.

9. A fluid line connection assembly according to claim 1, wherein:

one of said first mating structure and said second mating structure includes an annular channel; and the other of said first mating structure and said second mating structure includes a cylinder dimensioned to fit inside said annular channel.

10. A fluid line connection assembly according to claim 9, wherein:

said first mating structure and said second mating structure are sonically welded.

11. A fluid line connection assembly according to claim 1, wherein:

said valve member support includes a plurality of vanes extending substantially the entire length of said cylindrical chamber.

12. A fluid line connection assembly according to claim 1, wherein:

said first fluid coupling member includes one of a Y-site adapter, an IV manifold and a male luer.

* * * * *